(12) United States Patent
Fox et al.

(10) Patent No.: US 9,791,362 B2
(45) Date of Patent: Oct. 17, 2017

(54) FLUID MIXING AND RINSING SYSTEM FOR A FLOW CYTOMETER

(71) Applicant: Bio-Rad Laboratories, Inc., Hercules, CA (US)

(72) Inventors: Daniel Nelson Fox, Bellvue, CO (US); Nathan Michael Gaskill-Fox, Fort Collins, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/417,131

(22) Filed: Jan. 26, 2017

(65) Prior Publication Data

US 2017/0136430 A1    May 18, 2017

Related U.S. Application Data

(62) Division of application No. 13/922,635, filed on Jun. 20, 2013.

(60) Provisional application No. 61/663,021, filed on Jun. 22, 2012.

(51) Int. Cl.
*G01N 15/14* (2006.01)

(52) U.S. Cl.
CPC .................... *G01N 15/14* (2013.01)

(58) Field of Classification Search
CPC ..................... B01F 3/088; G01N 15/1404
See application file for complete search history.

(56) References Cited

U.S. PATENT DOCUMENTS

| | | | |
|---|---|---|---|
| 3,826,364 A | 7/1974 | Bonner et al. | |
| 4,284,210 A | 8/1981 | Horak | |
| 5,641,457 A | 6/1997 | Vardanega et al. | |
| 5,891,734 A * | 4/1999 | Gill ........................ | B01F 5/0453 422/63 |
| 5,915,925 A | 6/1999 | North, Jr. | |
| 6,183,697 B1 | 2/2001 | Tanaka et al. | |
| 6,200,101 B1 | 3/2001 | North, Jr. | |
| 6,372,506 B1 | 4/2002 | Norton | |
| 7,242,474 B2 | 7/2007 | Cox et al. | |
| 7,776,268 B2 | 8/2010 | Rich | |

(Continued)

FOREIGN PATENT DOCUMENTS

| | | |
|---|---|---|
| CN | 1085330 | 4/1994 |
| CN | 1767891 | 5/2006 |

(Continued)

OTHER PUBLICATIONS

Chinese Second Office Action dated Dec. 20, 2016 issued in CN 201380030535.7.
Chinese Second Office Action dated Feb. 15, 2017 issued in CN 201380032476.7.
U.S. Appl. No. 15/376,504, filed Dec. 12, 2016, Fox et al.

(Continued)

*Primary Examiner* — David Sorkin
(74) *Attorney, Agent, or Firm* — Weaver Austin Villeneuve & Sampson LLP

(57) ABSTRACT

Disclosed is a system that can mix deionized water and concentrated sheath fluid to provide sheath fluid in a flow cytometer system having a desired concentration. Flow rates are low, which substantially match the flow rate of sheath fluid through the nozzle, so that turbulence and air bubbles are not formed in the sheath fluid. The available deionized water is then used for back flushing and removal of sample cells and deposited salts from the sheath fluid.

18 Claims, 3 Drawing Sheets

(56) References Cited

U.S. PATENT DOCUMENTS

| | | | |
|---|---|---|---|
| 8,004,674 | B2 | 8/2011 | Ball et al. |
| 8,229,684 | B2 | 7/2012 | Goebel et al. |
| 8,564,776 | B2 | 10/2013 | Graves et al. |
| 9,551,637 | B2 | 1/2017 | Fox et al. |
| 9,592,483 | B2 | 3/2017 | Fox et al. |
| 2002/0154567 | A1 | 10/2002 | Husher |
| 2002/0192113 | A1 | 12/2002 | Uffenheimer et al. |
| 2004/0031521 | A1 | 2/2004 | Vrane et al. |
| 2005/0019949 | A1 | 1/2005 | Hall et al. |
| 2005/0069454 | A1* | 3/2005 | Bell ............... B01L 9/54 422/68.1 |
| 2005/0123445 | A1* | 6/2005 | Blecka ........... G01N 35/0099 422/64 |
| 2005/0219945 | A1 | 10/2005 | Kelley et al. |
| 2008/0182056 | A1 | 7/2008 | Bakker et al. |
| 2010/0018584 | A1 | 1/2010 | Bransky et al. |
| 2010/0227323 | A1* | 9/2010 | Baeumner ........ G01N 27/44721 435/6.19 |
| 2010/0319469 | A1 | 12/2010 | Rich |
| 2011/0221892 | A1 | 9/2011 | Neckels et al. |
| 2012/0070818 | A1 | 3/2012 | Rowlen et al. |
| 2012/0097582 | A1 | 4/2012 | Tsukii et al. |
| 2013/0333765 | A1 | 12/2013 | Fox et al. |
| 2013/0343149 | A1 | 12/2013 | Fox et al. |

FOREIGN PATENT DOCUMENTS

| | | |
|---|---|---|
| CN | 201880510 U | 6/2011 |
| EP | 2224224 A2 | 9/2010 |
| WO | 2009/026919 A2 | 3/2009 |
| WO | 2010/132053 A1 | 11/2010 |
| WO | 2010/141096 A1 | 12/2010 |
| WO | 2013/188770 A1 | 12/2013 |
| WO | 2013/192401 A1 | 12/2013 |

OTHER PUBLICATIONS

U.S. Office Action dated Sep. 22, 2015 issued in U.S. Appl. No. 13/918,156.
U.S. Final Office Action dated Feb. 22, 2016 issued in U.S. Appl. No. 13/918,156.
U.S. Office Action dated May 26, 2016 issued in U.S. Appl. No. 13/918,156.
U.S. Notice of Allowance dated Sep. 28, 2016 issued in U.S. Appl. No. 13/918,156.
U.S. Notice of Allowance [Corrected Notice of Allowability] dated Oct. 18, 2016 issued in U.S. Appl. No. 13/918,156.
U.S. Office Action dated Mar. 3, 2016 issued in U.S. Appl. No. 13/922,635.
U.S. Notice of Allowance dated Sep. 23, 2016 issued in U.S. Appl. No. 13/922,635.
U.S. Notice of Allowance dated Oct. 27, 2016 issued in U.S. Appl. No. 13/922,635.
PCT International Search Report and Written Opinion, dated Nov. 14, 2013, issued in PCT/US2013/045902.
PCT International Preliminary Report on Patentability and Written Opinion, dated Dec. 24, 2014, issued in PCT/US2013/045902.
Chinese First Office Action dated Jan. 29, 2016 issued in CN 201380030535.7.
European Extended Search Report dated Jan. 7, 2016 issued in EP 13 80 4145.4.
PCT International Search Report and Written Opinion, dated Nov. 15, 2013, issued in PCT/US2013/046774.
PCT International Preliminary Report on Patentability and Written Opinion, dated Dec. 31, 2014, issued in PCT/US2013/046774.
European Extended Search Report dated Feb. 5, 2016 issued in EP 13 80 6142.9.
Chinese First Office Action dated Jun. 2, 2016 issued in CN 201380032476.7.

* cited by examiner

FLUID MIXING AND RINSING SYSTEM FOR A FLOW CYTOMETER

CROSS-REFERENCE TO RELATED APPLICATIONS

This application is a divisional application of U.S. patent application Ser. No. 13/922,635, filed on Jun. 20, 2013, entitled "FLUID MIXING AND RINSING SYSTEM FOR A FLOW CYTOMETER," which claims the benefit under 35 U.S.C. §119(e) to U.S. Provisional Patent Application No. 61/663,021, filed Jun. 22, 2012, entitled "Fluid Mixing and Rinsing System for a Flow Cytometer," which are both incorporated herein by reference for all that they disclose and teach.

This application is related to U.S. Provisional Patent Application Ser. No. 61/656,934, filed Jun. 7, 2012, by Daniel N. Fox, Susan Hunter, Nathan Michael Gaskill-Fox, Kevin P. Raley and Richard A. Miles, entitled "Automated and Accurate Drop Delay for Flow Cytometry," U.S. Provisional Patent Application Ser. No. 61/659,528, filed Jun. 14, 2012, by Daniel N. Fox and Nathan M. Gaskill-Fox, entitled "Flow Rate Balance, Dynamically Adjustable Sheath Delivery System for Flow Cytometry," U.S. Provisional Patent Application filed on the same date as the present application, by Nathan M. Gaskill-Fox, Daniel N. Fox and Rodney C. Harris, entitled "Two Station Sample and Washing System," U.S. Provisional Patent Application filed on the same date of the present application, by Daniel N. Fox, Matthias J. G. Ottenberg and Kevin P. Raley, entitled "Condensed Geometry Nozzle for Flow Cytometry," and U.S. Provisional Patent Application filed on the same date as the present application, by Nathan M. Gaskill-Fox, Daniel N. Fox and Rodney C. Harris, entitled "Multi-Directional Sorting with Reduced Contamination in a Flow Cytometer." All of these applications are hereby specifically incorporated herein by reference, for all that they disclose and teach.

BACKGROUND

Flow cytometers are useful devices for analyzing and sorting various types of particles in fluid streams. These cells and particles may be biological or physical samples that are collected for analysis and/or separation. The sample is mixed with a sheath fluid for transporting the particles through the flow cytometer. The particles may comprise biological cells, calibration beads, physical sample particles, or other particles of interest. Sorting and analysis of these particles can provide valuable information to both researchers and clinicians. In addition, sorted particles can be used for various purposes to achieve a wide variety of desired results.

SUMMARY

An embodiment of the present invention may therefore comprise a system for mixing deionized water and sheath fluid concentrate comprising: a first container that supplies deionized water; a second container that supplies concentrated sheath fluid; a pump that delivers the deionized water and the concentrated sheath fluid into a reservoir at a rate that is sufficiently slow that substantially no bubbles form in the pressurized reservoir; a valve that has a first input that is coupled to the deionized water in the first container, and supplies the deionized water through an output to the reservoir when the valve is in a first position, and a second input that is coupled to the concentrated sheath fluid in the second container, and supplies the deionized water through the output to the reservoir; a controller that places the valve in the first position until a predetermined amount of the deionized water is supplied to the pressurized container, and switches the valve to the second position until a predetermined amount of the concentrated sheath fluid is supplied to the reservoir, so that the predetermined amount of the deionized water and the predetermined amount of the concentrated sheath fluid creates a mixture having a desired concentration of sheath fluid.

An embodiment of the present invention may further comprise a method of mixing deionized water and concentrated sheath fluid in a flow cytometer comprising: supplying deionized water from a first container; supplying concentrated sheath fluid from a second container; pumping the deionized water and the concentrated sheath fluid into a reservoir at a rate that is sufficiently slow to substantially eliminate turbulence that causes bubbles to form in the reservoir; controlling a first valve that is connected to the first container in a first position and the second container in a second position so that the first valve is disposed in the first position until a predetermined amount of the deionized water is supplied to the reservoir and the first valve is disposed in the second position until a predetermined amount of the concentrated sheath fluid is supplied to the reservoir to produce sheath fluid having a predetermined concentration in the reservoir.

DETAILED DESCRIPTION OF THE EMBODIMENTS

Figure 1:
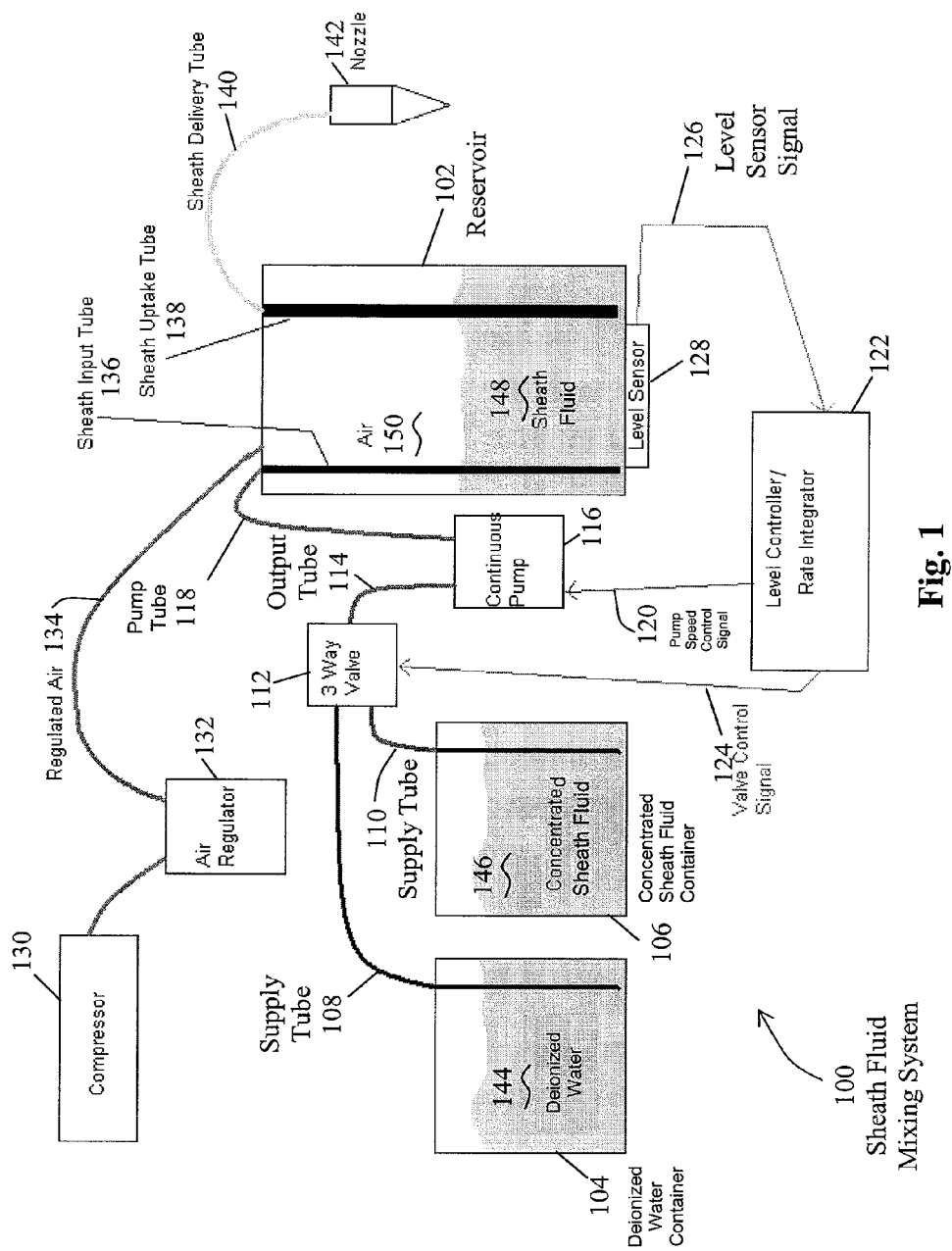
FIG. 1 is a schematic view of an embodiment of a sheath fluid mixing system.

FIG. 1 is schematic illustration of an embodiment of a sheath fluid mixing system 100. As illustrated in FIG. 1, deionized water 144 from a deionized water container 104, and concentrated sheath fluid 146 in concentrated sheath fluid container 106, are supplied to a three-way valve 112. The deionized water container 104 may be an unpressurized deionized water container that is accessible to a user, so that a user can remove the container and replace the container with a new container. Similarly, the concentrated sheath fluid container 106 is also accessible to a user, so that the user may remove the concentrated sheath fluid container 106 and replace it with a new concentrated sheath fluid container. Three-way valve 112 is controlled by a valve control signal 124 that is generated by a level controller/rate integrator 122. Continuous pump 116 draws either deionized water 144 or concentrated sheath fluid 146 through the three-way valve 112, depending upon the position of three-way valve 112.

Concentrated sheath fluid having a concentration of 8x has typically been used to reduce shipping costs and storage costs of sheath fluid by reducing the size and weight of the shipped product by a factor of 8x. Users of flow cytometers then mix the 8x concentrated sheath fluid with deionized water to create sheath fluid having the proper 1x concentration. However, if the deionized water and the sheath fluid concentrate are mixed at a rate that is not slow, turbulence is created and micro-bubbles are introduced into the mixture. These micro-bubbles can accumulate in the sheath fluid mixing system 100, illustrated in FIG. 1, and cause problems in the operation of the flow cytometer. As a result, users are typically instructed to mix the concentrated sheath fluid and the deionized water at least a day or more before use. This is normally an impractical solution and requires additional labor on the part of the user. Operator usability of the system and automation of the processes that eliminate manual labor are advantageous.

Since supplies of concentrated sheath fluid are readily available to users and the concentrated sheath fluid is less costly to ship and store, it is desirable to provide a way to use the concentrated sheath fluid. Further, most laboratories that use flow cytometers have sources of deionized water that can be mixed with the concentrated sheath fluid. If not, pre-packaged supplies of deionized water are available. The system illustrated in FIG. 1 uses the three-way valve 112 to slowly mix the deionized water 144 with the concentrated sheath fluid 146 by controlling the three-way valve 112 with the valve control signal 124, so that the three-way valve supplies a predetermined amount of deionized water 144 and a predetermined amount of the concentrated sheath fluid 146 to provide a supply of sheath fluid that has the proper (1x) concentration. Continuous pump 116 pumps the deionized water 144 and concentrated sheath fluid 146 through the pump tube 118 and sheath input tube 136 to the reservoir 102. Reservoir 102 may be disposed in the flow cytometer, and not be readily removed by a user. The amounts of each of the respective fluids is small, so that the fluids disperse in the reservoir 102 to create a uniform concentration sheath fluid 148 which is 1x. For example, in one embodiment, a continuous pump 116 initially supplies fluid to the reservoir 102 at a rate of 8 mL per minute. This rate is designed to substantially match the outflow rate of sheath fluid 148 from the reservoir 102 through the sheath delivery tube 140 to the nozzle 142. By supplying fluid to the reservoir 102 at a rate that substantially matches the outflow of sheath fluid from the reservoir 102, a substantially constant level of sheath fluid 147 can be maintained in reservoir 102, as disclosed in more detail with respect to U.S. Patent Application Ser. No. 61/659,528, filed Jun. 14, 2012, by Daniel N. Fox and Nathan M. Gaskill-Fox, entitled "Flow Rate Balance, Dynamically Adjustable Sheath Delivery System for Flow Cytometry," which is specifically incorporated herein, by reference, for all that it discloses and teaches.

To create an in-flow of 8 mL per minute, three-way valve 112 provides 7 mL of the deionized water 144 and 1 mL of the concentrated sheath fluid 146. In this manner, 8 mL of fluid are supplied and the amount of the concentrated sheath fluid 146 is one-eighth of the total amount of fluid, and deionized water 144 is seven-eighths of the total amount of fluid. The total amount of 8 mL supplied allows the concentrated sheath fluid 146 to easily disperse within the much larger volume of sheath fluid 148 in the reservoir 102. Since the injection of the deionized water 144 and the concentrated sheath fluid 146 matches the outflow rate of sheath fluid 148 through nozzle 142, the injection occurs over a one minute period. The very slow rate of injection of the deionized water 144 and concentrated sheath fluid 146 into the reservoir 102, a total amount of 8 mL in a minute, results in virtually no turbulence and no bubbles being created in the sheath fluid 148. Level sensor 128 senses the level of the sheath fluid 148 in the reservoir 102 and generates a level sensor signal 126 that is supplied to the level controller/rate integrator 122. If the level of the sheath fluid 148 in the reservoir 102 is low or high, the rate at which fluid is pumped by the continuous pump 116 is adjusted by the level controller/rate integrator 122 using a pump speed controller signal 120. This is explained in more detail in the above-referenced patent application, entitled "Flow Rate Balance, Dynamically Adjustable Sheath Delivery System for Flow Cytometry."

FIG. 1 also discloses a compressor 130 that supplies compressed air to air regulator 132. The source of regulated air 134 is supplied to the reservoir 102 at a pressure of approximately 30 psi, in one embodiment. The pressurized air 150 in the reservoir 102 further regulates the amount of pressure on the fluid stream that is delivered through the sheath delivery tube 140 to nozzle 142. It is desirable to have a constant pressure of the sheath fluid 148 flowing through the nozzle 142 to accurately perform the processes of a flow cytometer. The pressure of air 150 in the reservoir 102 makes up for differences in the pressure of the fluid in the sheath delivery tube 140 that results from changes in the level of the sheath fluid 148, as set forth in the above-referenced patent application. The adjustment to the flow of the continuous pump 116 by the level controller/rate integrator 122 may affect the timing of the operation of the three-way valve 112. The level of the sheath fluid 148 in the reservoir 102 may change for various reasons. For example, continuous pump 116 may become air locked because of a bubble in the output tube 114. A purge process must then occur, and the level of the sheath fluid 148 may change by an amount that results in the continuous pump 116 running at a higher rate than the rate to normally maintain the level of the sheath fluid 148 substantially constant in the reservoir 102. In addition, the deionized water container 104 and concentrated sheath fluid container 106 may be hot swapped with new containers, which also causes the level of the sheath fluid 148 to decrease. Again, this is explained in more detail with respect to the above-referenced application entitled "Flow Rate Balance, Dynamically Adjustable Sheath Delivery System for Flow Cytometry."

Since the pressure of the sheath fluid 148 in the nozzle 142 should be closely maintained, any changes in the level of the sheath fluid 148 in reservoir 102 should be adjusted in a quick manner. Accordingly it is desirable to change the flow rate of the continuous pump 116 as soon as possible to make up for changes in the level of the sheath fluid 148 in the reservoir 102. As such, the level controller/rate integrator 122 tracks the amount of deionized water 144 supplied to the reservoir 102 until a predetermined amount has been delivered. Then, the three-way valve 112 is changed to close the port for the supply tube 108 and open the port for the supply tube 110 to pump the concentrated sheath fluid 146 into the reservoir 102 until a predetermined amount of the concentrated sheath fluid 146 is pumped into the reservoir 102 to create the proper ratio and proper concentration. For example, the level controller/rate integrator 122 generates a valve control signal 124 to pump deionized water 144 into reservoir 102. The level controller/rate integrator 122 generates a pump speed control signal 120 based upon the level sensor signal 126 generated by the level sensor 128. If the sheath fluid 148 is low, the level sensor 128 detects the low level and generates a level sensor signal 126, that is read by the level controller/rate integrator 122, which generates the pump speed control signal 120 to increase the flow rate of the continuous pump 116.

The level controller/rate integrator 122, illustrated in FIG. 1, tracks the amount of deionized water 144 pumped by the continuous pump 116 into the reservoir 102 by integrating the pump speed of the continuous pump 116 over time. In one embodiment, when it is determined that 7 mL of deionized water 144 has been pumped by the continuous pump 116, a valve control signal 124 is generated to switch to the supply tube 110 to provide concentrated sheath fluid 146. The level controller/rate integrator 122 integrates the pump rate of the continuous pump 116 over time until 1 mL of concentrated sheath fluid 146 has been pumped by the continuous pump 116. At that point, the level controller/rate integrator 122 generates a valve control signal 124 to switch the three-way valve, so that deionized water 144 is being pumped by the continuous pump 116. This process continues. In this manner, the concentration of the sheath fluid 148 in the reservoir 102 does not change, since the proper ratio of fluids is supplied to the reservoir 102. When the continuous pump 116 is pumping at higher rates to increase the level of the sheath fluid 148 in the reservoir 102, the time periods for switching the three-way valve 112 are reduced. Similarly, if the level of the sheath fluid 148 in the reservoir 102 is above the preset level, the continuous pump 116 has a reduced flow rate and the time periods for switching the three-way valve 112 are increased.

Figure 2:
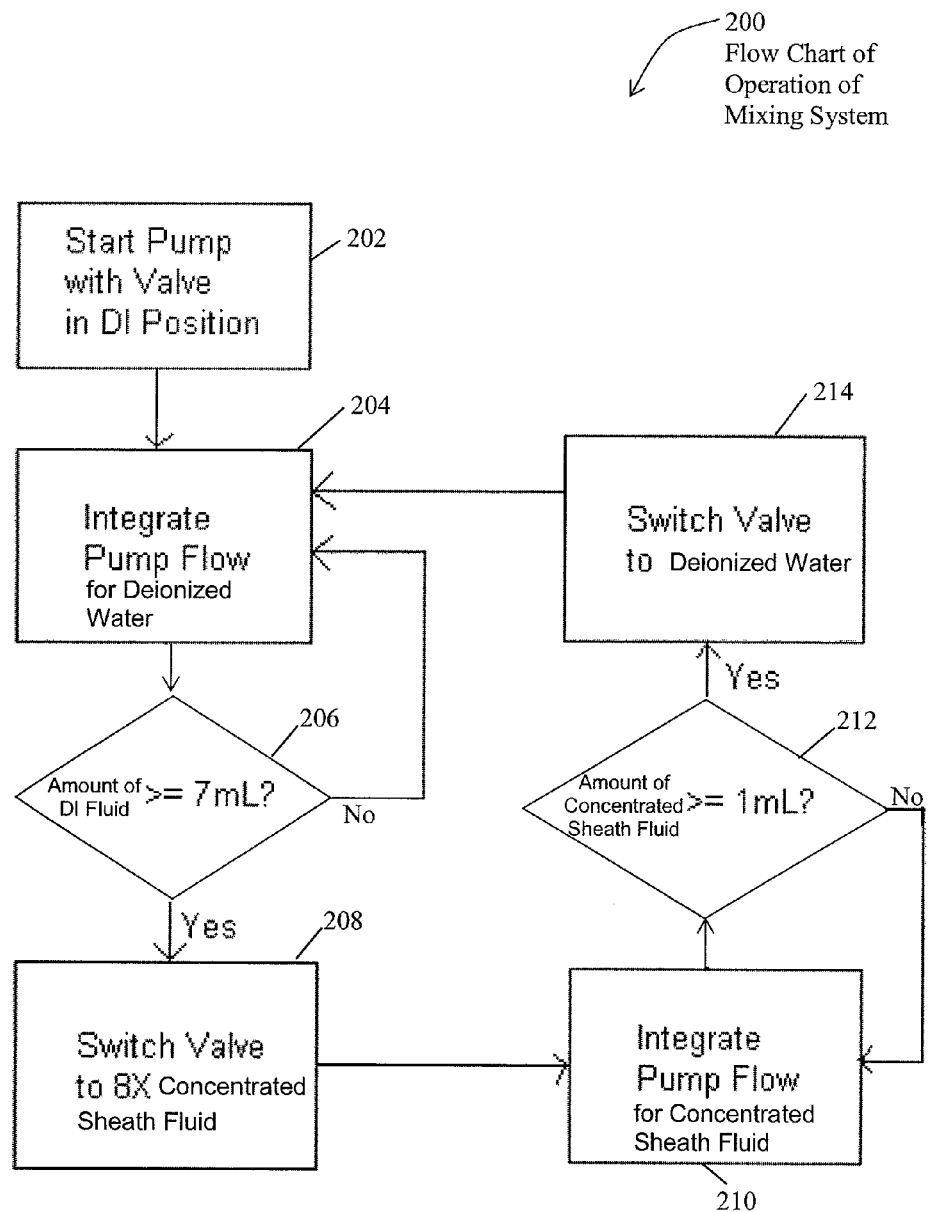
FIG. 2 is a flow diagram illustrating the operation of the three-way valve illustrated in FIG. 1.

FIG. 2 is a flow chart 200 of the operation of the system illustrated in FIG. 1. At step 202, the level controller/rate integrator 122 places the three-way valve 112 is a position so that deionized water 144 is being pumped from the deionized water container 104. At step 204, the pump flow rate is integrated over time to determine the amount of deionized water that has been pumped by the continuous pump 116. For example, in one embodiment, the pump rate is summed at 20 ns intervals. The sum of the pump rate over the 20 ns intervals indicates the amount of fluid that has been pumped by the continuous pump 116. For example, at 8 mL per minute, each 20 ns interval accounts for approximately 160 pL. If 25 million intervals at 20 ns are summed together, which would amount to 0.5 seconds, the sum would be 4 mL. When the target amount is reached, the level controller/rate integrator 122 generates a valve control signal 124 to change the three-way valve 112 to pump the concentrated sheath fluid 146. Accordingly, at step 206, it is determined whether the amount of fluid, in this case the deionized water 144, is greater than or equal to 7 mL. If not, the process continues to integrate the pump flow at step 204. If the amount of deionized water has reached 7 mL, the process proceeds to step 208. At step 208, the valve control signal 124 is generated to switch the three-way valve 112 to the concentrated sheath fluid 146. The process then proceeds to step 210, where the level controller/rate integrator 122 integrates the pump flow for the concentrated sheath fluid 146. The sampling can take place at the 20 ns rate, as set forth above, or at any desired rate. Further, any integration period can be used to provide an accurate number for the amount of concentrated sheath fluid delivered by pump 116. At step 212, it is determined whether the amount of concentrated sheath fluid is greater than or equal to 1 mL. If not, the process returns to step 210. If the amount is greater than or equal to 1 mL, the level controller/rate integrator 122 generates a valve control signal 124 to switch the three-way valve 112 to pump deionized water at step 214. The process then returns to step 204 to integrate the pump flow for the deionized water.

Accordingly, the level controller/rate integrator 122 generates a valve control signal 124 that switches the three-way valve 112 between supply tube 108 that supplies the deionized water 144 and supply tube 110 that supplies the concentrated sheath fluid 146. The valve control signal 124 is generated when the integrated amount of flow, as detected by level controller/rate integrator 122, reaches a predetermined amount for each of the fluids. In the present instance, the amounts of 7 mL of the deionized water 144 and 1 mL of the concentrated sheath fluid 146 are used as the predetermined amounts to achieve the proper concentration of mixed fluid. Other amounts can be used.

Figure 3:
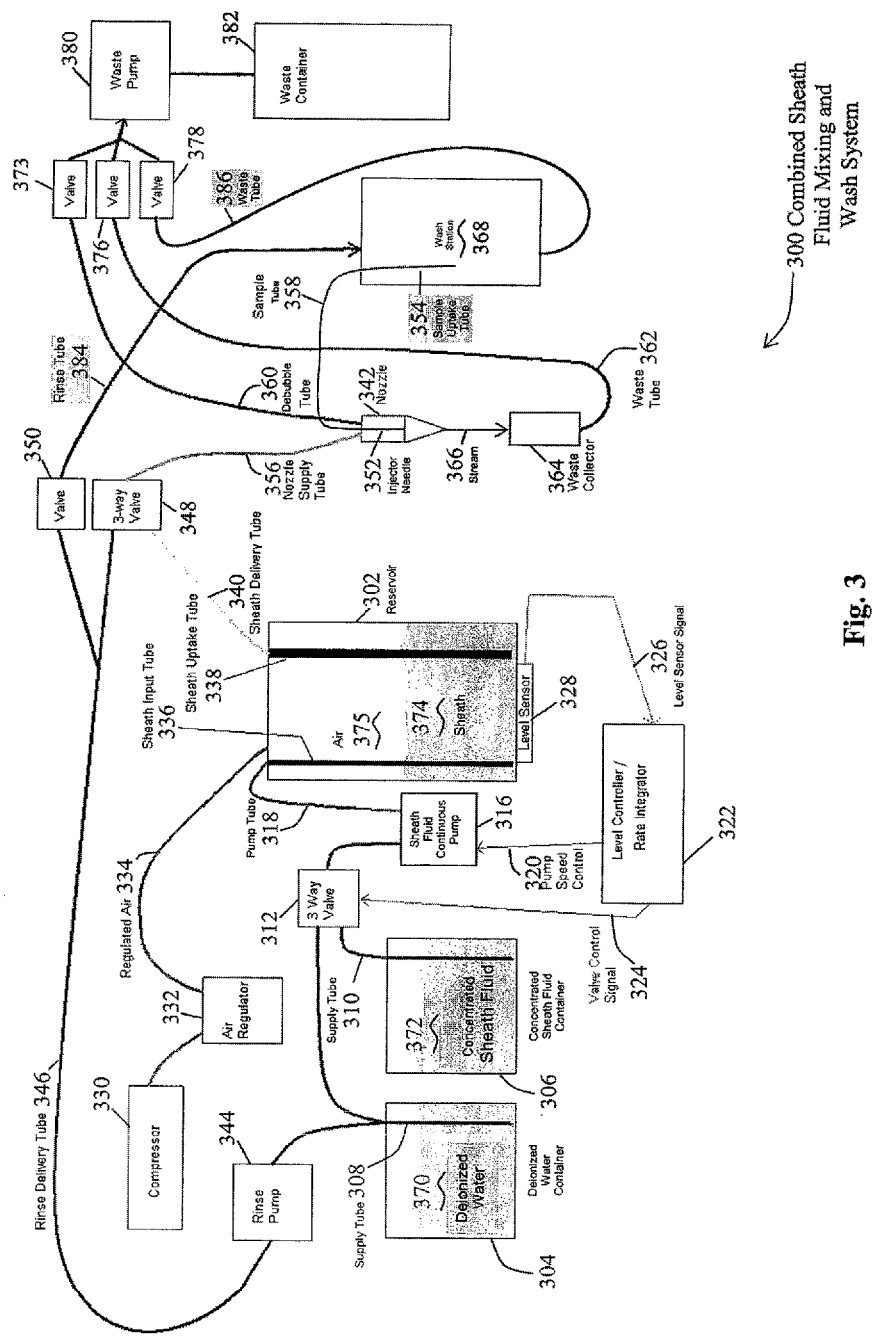
FIG. 3 is a schematic illustration of a combined sheath fluid mixing system and wash system.

FIG. 3 is a schematic illustration of a combined sheath fluid mixing and wash system 300. As illustrated in FIG. 3, reservoir 302 contains a sheath fluid 374 and pressurized air 375. The deionized water container 304 provides a supply of deionized water 370. Concentrated sheath fluid container 306 provides a supply of concentrated sheath fluid 372. Three-way valve 312 is connected to supply tube 308, that is disposed in deionized water container 304, and supply tube 310, is disposed in concentrated sheath fluid container 306. The level controller/rate integrator 322 generates a valve control signal 324 that operates the three-way valve 312 to select either supply tube 308 or supply tube 310. Continuous pump 316 operates in response to the pump control signal 320 to provide a continuous flow of sheath fluid into the reservoir 302, via pump tube 318, and sheath input tube 336. Level sensor 328 senses the level of the sheath fluid 374 in the reservoir 302 and generates a level sensor signal 326 that is applied to the level controller/rate integrator 322. The pump control signal 320 controls the continuous pump 316 to generally match the in-flow of sheath fluid through pump tube 318 to the outflow of sheath fluid 374 through sheath uptake tube 338 and sheath delivery tube 340. If the level of the sheath fluid 374 is below a certain predetermined level, the pump speed control signal 320 increases the pumping rate of the continuous pump 316, so that the desired level of the sheath fluid 374 can be re-established in the reservoir 302. Similarly, if the level of the sheath fluid 374 in the reservoir 302 is too high, the pump rate of the continuous pump 316 is reduced.

As also illustrated in FIG. 3, compressor 330 provides compressed air to air regulator 332. The regulated air 334, at the output of the air regulator 332, is applied to the reservoir 302 to maintain a supply of pressurized air 375 in the reservoir 302. The air pressure of air 375 is also regulated to maintain a substantially constant pressure of sheath fluid 374 in the sheath delivery tube 340, as described in more detail with respect to the above-identified application entitled "Flow Rate Balance, Dynamically Adjustable Sheath Delivery System for Flow Cytometry." Since the sheath fluid 374 is under pressure, the sheath fluid flows through the sheath uptake tube 338 and sheath delivery tube 340 to the three-way valve 348. These devices described in FIG. 3 operate in the same manner as the devices illustrated in FIG. 1, to provide the proper concentration of the sheath fluid 374, which is maintained by pumping the proper amounts of deionized water 370 and concentrated sheath fluid 372 into the reservoir 302 by controlling the three-way valve 312. Again, the pump rate of the continuous pump 316 is integrated over short time periods to determine and control the amount of fluid delivered from each container 304, 306. In this manner, the proper concentration of sheath fluid 374 is maintained in the reservoir 302.

FIG. 3 also illustrates a cleaning cycle that utilizes the deionized water 370 in the unpressurized external deionized water container 304. Deionized water can perform a substantially better job of cleaning internal parts that have been in contact with sample fluid and sheath fluid. For convenience, most systems simply use sheath fluid for cleaning parts of a flow cytometer that have contacted sample fluid. As illustrated in FIG. 3, rather than using sheath fluid, the deionized water 370 can be used that is available in the deionized water container 304.

Deionized water is excellent fluid for dissolving solids that have formed from sheath fluid, such as deposited salts, and also kills and removes many cells that could cause contamination of a subsequent sample to be sorted. Cells typically die because the cellular process attempts to balance the salt concentration inside the cell with the environment of the fluid in which the cell is disposed. In a deionized water environment, cells absorb water to balance the salt concentration of the cells with the deionized water, which does not contain any salt. Cells absorb water so quickly, in an attempt to reduce salt concentration, that the cells burst and die. For these reasons, deionized water is a preferred rinsing fluid.

As shown in FIG. 3, the combined sheath fluid mixing and washing system 300 provides an available source of deionized water 370 in the deionized water container 304. The deionized water 370 can then be used for both dissolving salt deposits from the sheath fluid that may accumulate on parts of the system that contact sheath fluid, and kill and remove cells that may have deposited or collected in the flow cytometer.

During a wash phase, rinse pump 344 is activated to deliver deionized water 370 via rinse delivery tube 346. Deionized water is applied to a first input port of a three-way valve 348. A second input port of the three-way valve 348 is connected to the sheath delivery tube 340, which supplies sheath fluid 374 from the sheath uptake tube 338 to the nozzle supply tube 356 during a sample cycle. During the wash cycle, the three-way valve delivers deionized water 370 through the nozzle supply tube 356, which is connected to the nozzle cavity of the nozzle 342. The deionized water is inserted into the nozzle cavity of nozzle 342 under pressure, to create a stream 366 of deionized water that flows into the waste collector 364. Any deposited salts from the sheath fluid in the nozzle 342, including the opening at the bottom of nozzle 342, are dissolved and rinsed by stream 366. The stream 366 of deionized water flows through the waste collector 364, dissolving any salts that are deposited in the waste collector 364, and are disposed of by waste tube 362 through valve 376 and pumped by the waste pump 380 into the waste container 382. The rinse delivery tube 346 also supplies deionized water 370 to the valve 350. When the valve 350 is opened, deionized water flows through the rinse tube 384. The deionized water is sprayed around the outside of the sample uptake tube 354 to remove and kill any sample cells that may exist on the outside surface of the sample uptake tube 354, as disclosed in more detail with respect to the above-identified application entitled "Flow Rate Balance, Dynamically Adjustable Sheath Delivery System for Flow Cytometry."

As also shown in FIG. 3, waste pump 380 then draws the deionized water 370 through the waste tube 386 and valve 378 for deposit into the waste container 382. In addition, the pressure of the deionized water 370 in the nozzle 342, created by the rinse pump 344, causes the deionized water to flow backwards through the injector needle 352, into the sample tubing 358. Any sample that is left in the injector needle 352 is backwashed through the sample tubing 358 and backwards through the sample uptake tube 354. Any sample fluid that remains in the sample tubing 358, or the sample uptake tube 354, is backwashed into the wash station 368. Any sample cells left from the sampling process are killed and drained through waste tube 386, valve 378, and pumped by the waste pump 380 into the waste container 382. Additionally, deionized water 370 backflows through the de-bubble tube 360 and through valve 373 to the waste pump 380, which disposes of the fluid in waste container 382.

Hence, the mixing system illustrated in FIG. 3 allows for accurate mixing at low flow rates to supply a sheath fluid of a proper concentration into the reservoir 302. The low flow rates do not substantially create any turbulence or bubbles in the sheath fluid 374. Accurate concentrations can be established by integrating the pump rate to determine the amount of fluid that has flowed from each of the containers 304, 306. By using concentrated sheath fluid, the cost of shipping the sheath fluid is substantially reduced. Deionized water can be easily generated at the location of the flow cytometer. The supply of deionized water in the system allows for convenient and easy washing to both clear and kill sample cells and remove accumulated salts on various portions of the flow cytometer system. All of the paths that are typically exposed to sheath fluid and air that could dry and form deposits can be fully washed with the deionized water. The deionized water scours the deposits and cleans the system to prevent deposits or crystals from causing problems and kills and eliminates sample cells that may cause contamination. Because of the low flow rate, the deionized water and the concentrated sheath fluid are mixed in a manner that does not create turbulence or bubbles.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of mixing deionized water and concentrated sheath fluid in a flow cytometer comprising:
   supplying deionized water from a first container;
   supplying concentrated sheath fluid from a second container;
   pumping the deionized water and the concentrated sheath fluid into a reservoir at a rate that is sufficiently slow to substantially eliminate turbulence that causes bubbles to form in the reservoir; and
   controlling a first valve that is connected to the first container in a first position and the second container in a second position so that the first valve is disposed in the first position until a predetermined amount of the deionized water is supplied to the reservoir and the first valve is disposed in the second position until a predetermined amount of the concentrated sheath fluid is supplied to the reservoir to produce sheath fluid having a predetermined concentration in the reservoir.

2. The method of claim 1 wherein controlling the first valve comprises:
   sampling a pump control signal to generate a sampled pump control signal;
   summing the sampled pump control signal when the first valve is in the first position to determine when the predetermined amount of the deionized water has been delivered to the reservoir; and
   summing the sampled pump control signal when the first valve is in the second position to determine when the predetermined amount of the concentrated fluid has been delivered to the reservoir.

3. The method of claim 2 wherein the process of pumping the deionized water and the concentrated sheath fluid comprises:

pumping the deionized water and the concentrated sheath fluid at a rate that substantially matches an outflow rate of sheath fluid to the reservoir and a rate sufficient to establish, re-establish, and maintain a substantially constant level of the sheath fluid in the reservoir.

4. The method of claim 1 further comprising:
pumping the sheath fluid with a rinse pump to provide a supply of deionized water for cleaning parts that contact the sheath fluid and sample fluid in the flow cytometer;
applying the supply of deionized water to a nozzle in the flow cytometer so that the deionized water flows out of the nozzle into a waste collector to rinse the nozzle and the waste collector with the deionized water; and
applying the supply of deionized water to the nozzle to cause the deionized water to backwash an injector needle, a sample tube and a sample uptake tube to remove sheath fluid and sample particles.

5. A method for mixing deionized water in a first container and sheath fluid concentrate with a first concentration in a second container, the method comprising:
pumping, using a pump that is fluidically interposed between a valve and a pressurized reservoir, deionized water in the first container and concentrated sheath fluid in the second container into the pressurized reservoir at a flowrate that is sufficiently slow that substantially no bubbles form in the pressurized reservoir, wherein the valve has a first input that is fluidically coupled to the first container, wherein the valve has a second input that is fluidically coupled to the second container, wherein the valve is configured to allow deionized water in the first container to flow through an output to the pressurized reservoir when in a first position, and wherein the valve is configured to allow concentrated sheath fluid in the second container to flow through the output to the pressurized reservoir when in a second position; and
maintaining a concentration of a mixture of the deionized water and the concentrated sheath fluid in the pressurized reservoir such that the mixture has a concentration of sheath fluid less than the first concentration by repeatedly switching the valve between the first position, thereby supplying a first amount of deionized water by the pump to the pressurized reservoir, and the second position, thereby supplying a second amount of concentrated sheath fluid by the pump to the pressurized reservoir.

6. The method of claim 5, further comprising flowing the mixture out of the pressurized reservoir at an outflow rate, wherein pumping the deionized water in the first container and the concentrated sheath fluid in the second container into the pressurized reservoir is at a flowrate that is substantially equal to the outflow rate out of the pressurized reservoir.

7. The method of claim 6, further comprising:
generating, using a level sensor, a level sensor signal that is representative of a level of the mixture in the pressurized reservoir, and
changing, based on the level sensor signal from the level sensor, the flowrate of the pump.

8. The method of claim 7, wherein changing the flowrate of the pump further comprises determining that the level of the mixture in the pressurized reservoir is below a first level and increasing, based on the determination, the flowrate of the pump.

9. The method of claim 7, wherein changing the flowrate of the pump further comprises determining that the level of the mixture in the pressurized reservoir is above a second level and decreasing, based on the determination, the flowrate of the pump.

10. The method of claim 5, further comprising pumping, using a rinse pump fluidically connected to the first container and fluidically interposed between a second valve and the first container, deionized water in the first container to the second valve and to a nozzle of a flow cytometer, wherein the nozzle is fluidically connected to the second valve, and wherein the second valve is fluidically interposed between the nozzle and the rinse pump.

11. The method of claim 10, further comprising pumping, using the rinse pump, deionized water in the first container to one or more components selected from the group of: an injector needle, a sample tube, and a sample uptake tube, wherein each of the one or more components are fluidically connected to the second valve.

12. The method of claim 10, wherein pumping, using the rinse pump, deionized water in the first container to the nozzle further comprises pumping deionized water to a waste collector fluidically connected to the nozzle, wherein the nozzle is fluidically interposed between the second valve and the waste collector.

13. The method of claim 12, further comprising pumping, using a waste pump fluidically interposed between the waste collector and a waste container, material in the waste collector to the waste container.

14. The method of claim 5, wherein maintaining a concentration of a mixture of the deionized water and the concentrated sheath fluid in the pressurized reservoir further comprises maintaining a concentration of a mixture that is nominally seven parts deionized water to one part concentrated sheath fluid.

15. The method of claim 5, wherein pumping deionized water in the first container and concentrated sheath fluid in the second container into the pressurized reservoir at a flowrate further comprises a flowrate of about 8 milliliters per minute.

16. The method of claim 5, wherein:
the first amount is about 7 milliliters of deionized water, and
the second amount is about 1 milliliter of concentrated sheath fluid.

17. The method of claim 5, further comprising:
sampling a pump control signal;
creating a sampled pump control signal; and
summing the sampled pump control signal to determine when the first amount of deionized water has been delivered to the pressurized container and to determine when the second amount of concentrated sheath fluid has been delivered to the pressurized container.

18. The method of claim 17, further comprising generating, based on the determination, a valve control signal to cause the valve to switch between the first position and the second position.

* * * * *